(12) United States Patent
Wakisaka et al.

(10) Patent No.: US 11,653,882 B2
(45) Date of Patent: May 23, 2023

(54) SENSOR DATA CORRECTION SYSTEM

(71) Applicant: Hitachi, Ltd., Tokyo (JP)

(72) Inventors: Yoshihiro Wakisaka, Tokyo (JP); Nobuyuki Sugii, Tokyo (JP); Noriyuki Haga, Tokyo (JP); Tetsuya Ishimaru, Tokyo (JP); Hiroyuki Yoshimoto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 522 days.

(21) Appl. No.: 16/808,892

(22) Filed: Mar. 4, 2020

(65) Prior Publication Data

US 2021/0000425 A1 Jan. 7, 2021

(30) Foreign Application Priority Data

Jul. 5, 2019 (JP) .............................. JP2019-126108

(51) Int. Cl.
*A61B 5/00* (2006.01)
*A61B 5/11* (2006.01)
*G01L 5/00* (2006.01)
*G01P 13/00* (2006.01)

(52) U.S. Cl.
CPC .............. *A61B 5/7214* (2013.01); *A61B 5/11* (2013.01); *A61B 5/6843* (2013.01); *A61B 5/742* (2013.01); *A61B 5/746* (2013.01); *G01L 5/00* (2013.01); *G01P 13/00* (2013.01); *A61B 2562/0252* (2013.01)

(58) Field of Classification Search
CPC ....... A61B 5/7214; A61B 5/11; A61B 5/6843; A61B 5/742; A61B 5/746; A61B 2562/0252; A61B 2560/0228; A61B 2560/0238; A61B 2562/0219; A61B 5/1122; A61B 5/6806; A61B 5/1036; G01L 5/00; G01P 13/00
See application file for complete search history.

(56) References Cited

U.S. PATENT DOCUMENTS

| | | | | |
|---|---|---|---|---|
| 11,253,173 | B1* | 2/2022 | Demiralp | A61B 5/1122 |
| 11,367,519 | B1* | 6/2022 | Heldman | A61B 5/7246 |
| 11,457,874 | B2* | 10/2022 | Biederman | G06F 1/1652 |
| 2018/0345128 | A1 | 12/2018 | Ahmed et al. | |

(Continued)

FOREIGN PATENT DOCUMENTS

| | | |
|---|---|---|
| JP | 2000-505555 A | 5/2000 |
| JP | 2013-3782 A | 1/2013 |

(Continued)

OTHER PUBLICATIONS

Extended European Search Report received in corresponding European Application No. 20161379.1 dated Nov. 11, 2020.

*Primary Examiner* — May A Abouelela
(74) *Attorney, Agent, or Firm* — Mattingly & Malur, PC

(57) ABSTRACT

A sensor data correction system, includes: a standard motion mechanism unit for performing a standard motion of a wearable sensor; a determination unit calculating a relationship between first sensor data that is sensed by a first wearable sensor provided with the standard motion mechanism unit and second sensor data that is sensed by a second wearable sensor provided with the standard motion mechanism unit; and a correction unit correcting the first sensor data or the second sensor data, on the basis of the relationship that is calculated by the determination unit.

7 Claims, 15 Drawing Sheets

(56) References Cited

U.S. PATENT DOCUMENTS

| | | | |
|---|---|---|---|
| 2019/0170546 A1 | 6/2019 | Youssef et al. | |
| 2021/0141443 A1* | 5/2021 | Fukumoto | ............... G06T 7/251 |
| 2021/0196189 A1* | 7/2021 | Yazigi | .................. A61B 5/4818 |
| 2021/0259642 A1* | 8/2021 | Maeda | ................... G16H 50/80 |
| 2021/0275103 A1* | 9/2021 | Ishikawa | ................. A61B 5/725 |
| 2022/0160299 A1* | 5/2022 | Jessop | ................ G09B 19/0038 |

FOREIGN PATENT DOCUMENTS

| | | |
|---|---|---|
| JP | 2016-099398 A | 5/2016 |
| JP | 2017-156164 A | 9/2017 |

\* cited by examiner

FIG. 4
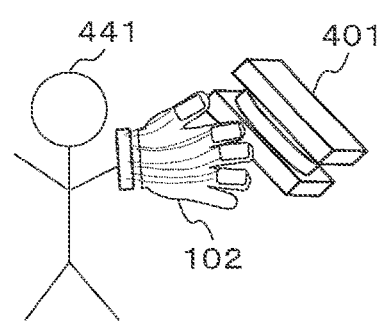
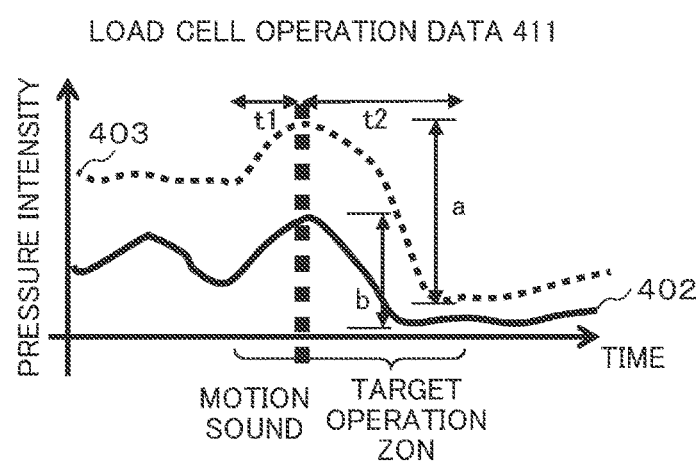
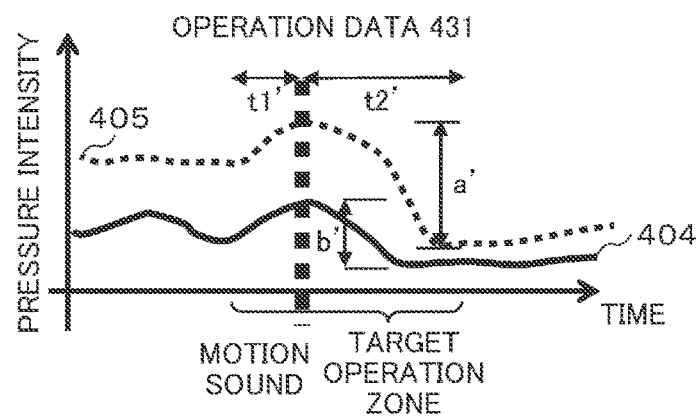

F I G. 10
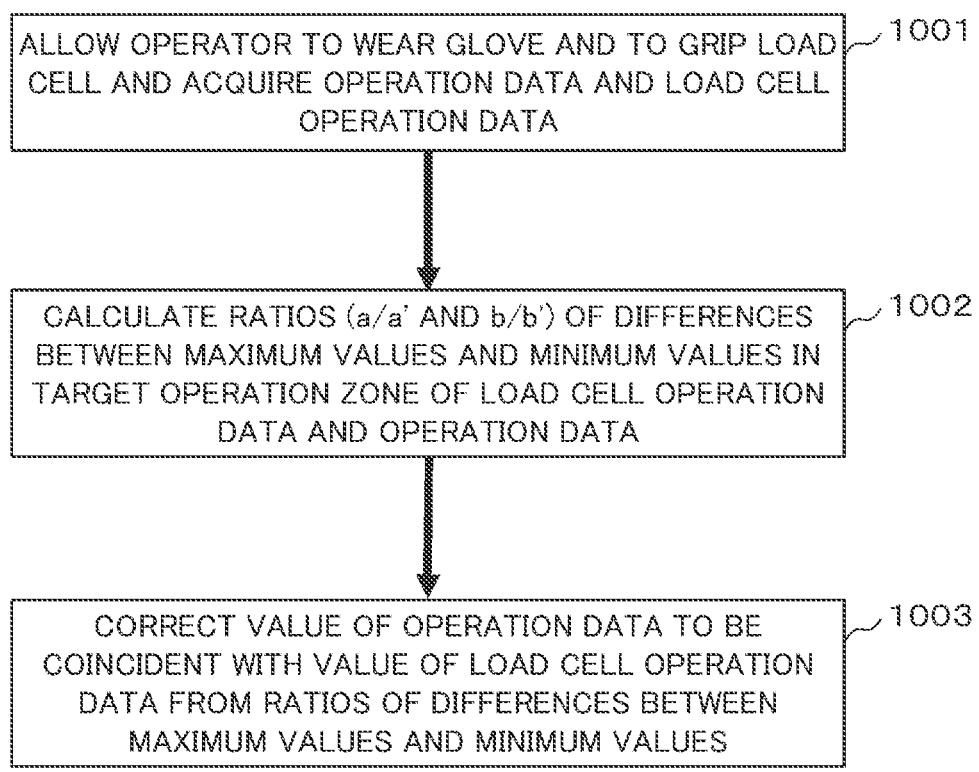

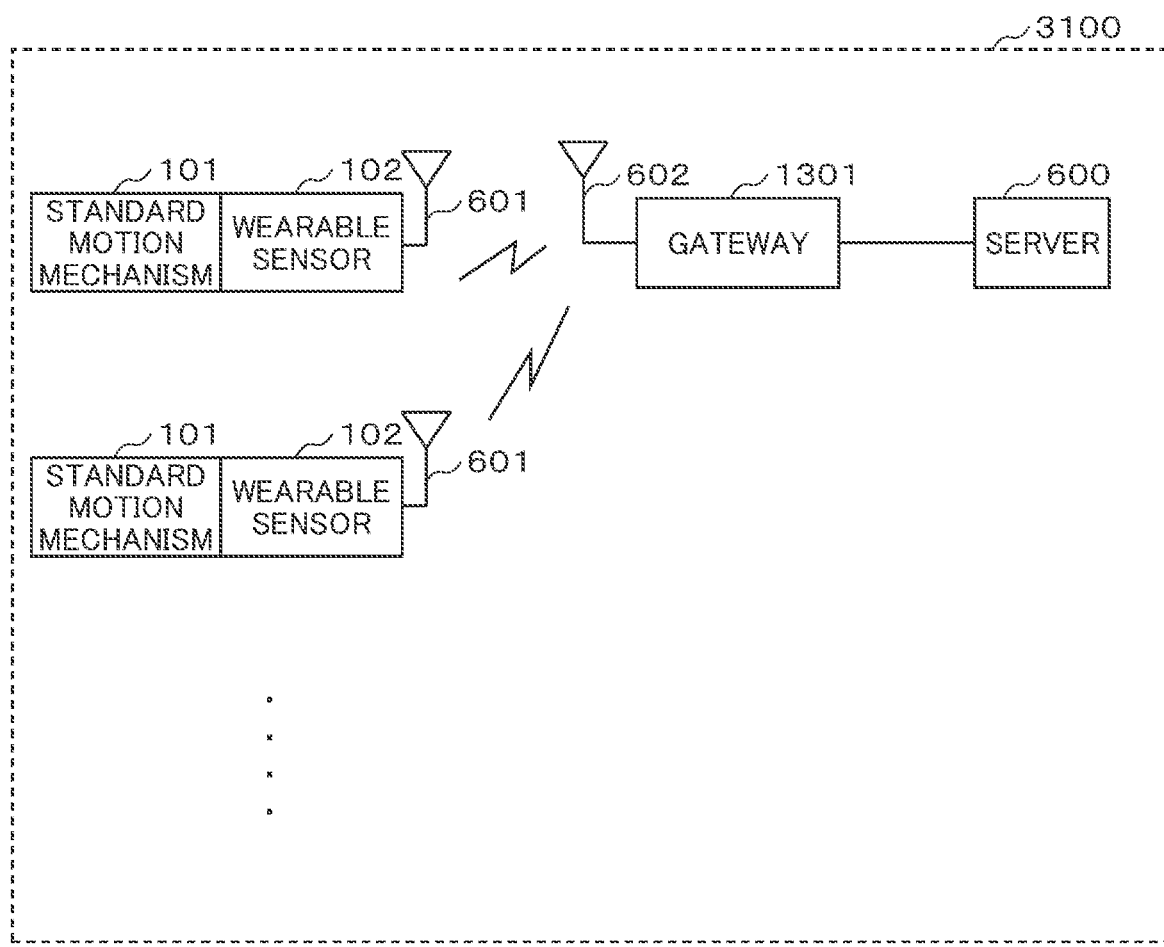
F I G. 1 3

SENSOR DATA CORRECTION SYSTEM

CROSS-REFERENCE TO RELATED APPLICATION

The present application claims priority from Japanese application JP2019-126108, filed on Jul. 5, 2019, the contents of which is hereby incorporated by reference into this application.

BACKGROUND OF THE INVENTION

1. Field of the Invention

The present invention relates to a sensor data correction system.

2. Description of the Related Art

For example, in Japanese Patent Application No. 2016-99398, a system, a method, and a program in which sensing data that is output from a motion sensor is recalculated on the basis of a coordinate point difference are disclosed as a system correcting an individual difference of sensing data. In the system, the method, and the program, data different from a target sensor is acquired, and the value of target sensor data is corrected on the basis of the value of the data.

In Japanese Patent Application No. 2016-99398, in order to obtain a more accurate result in consideration of an individual difference between people or sensors, error correction of the sensing data is performed by using a coordinate difference that is output from the motion sensor.

However, in wearable sensing, an aging property variation is large in accordance with material properties, an individual difference is large even in the same product, and an individual difference of a wearer is also large unlike a sensor of a device. For this reason, unless a personal difference of the wearer is known, it is not possible to interpret the data, and it is not possible to necessarily accurately correct the sensor data.

SUMMARY OF THE INVENTION

An object of the present invention is to provide a sensor data correction system that is capable of accurately correcting sensor data.

A sensor data correction system according to one aspect of the present invention is configured as a sensor data correction system, including: a standard motion mechanism unit for performing a standard motion of a wearable sensor; a determination unit calculating a relationship between first sensor data that is sensed by a first wearable sensor provided with the standard motion mechanism unit and second sensor data that is sensed by a second wearable sensor provided with the standard motion mechanism unit; and a correction unit correcting the first sensor data or the second sensor data, on the basis of the relationship that is calculated by the determination unit.

In addition, a sensor data correction system according to one aspect of the present invention is configured as a sensor data correction system, including: a standard motion mechanism unit for performing a standard motion of a wearable sensor; a determination unit calculating a relationship between standard sensor data that is sensed by the wearable sensor provided with the standard motion mechanism unit and sensor data that is sensed by the wearable sensor worn by an operator; and a correction unit correcting the sensor data or the standard sensor data, on the basis of the relationship that is calculated by the determination unit.

In addition, a sensor data correction system according to one aspect of the present invention is configured as a sensor data correction system, including: a load cell sensing a received pressure; a determination unit calculating a relationship between first sensor data that is sensed by a wearable sensor worn by an operator and second sensor data in which the load cell senses a pressure from the wearable sensor; and a correction unit correcting the first sensor data or the second sensor data, on the basis of the relationship that is calculated by the determination unit.

According to one aspect of the present invention, it is possible to accurately correct sensor data.

BRIEF DESCRIPTION OF THE DRAWINGS

FIG. 4 is an example of a mode for correcting an aging variation of the wearable sensor;

FIG. 10 is an example of a flowchart of correcting time degradation;

FIG. 13 is an example of a configuration in which the wearable sensor, a gateway, and a server are provided in the same factory or building;

DETAILED DESCRIPTION OF THE PREFERRED EMBODIMENTS

Figure 1:
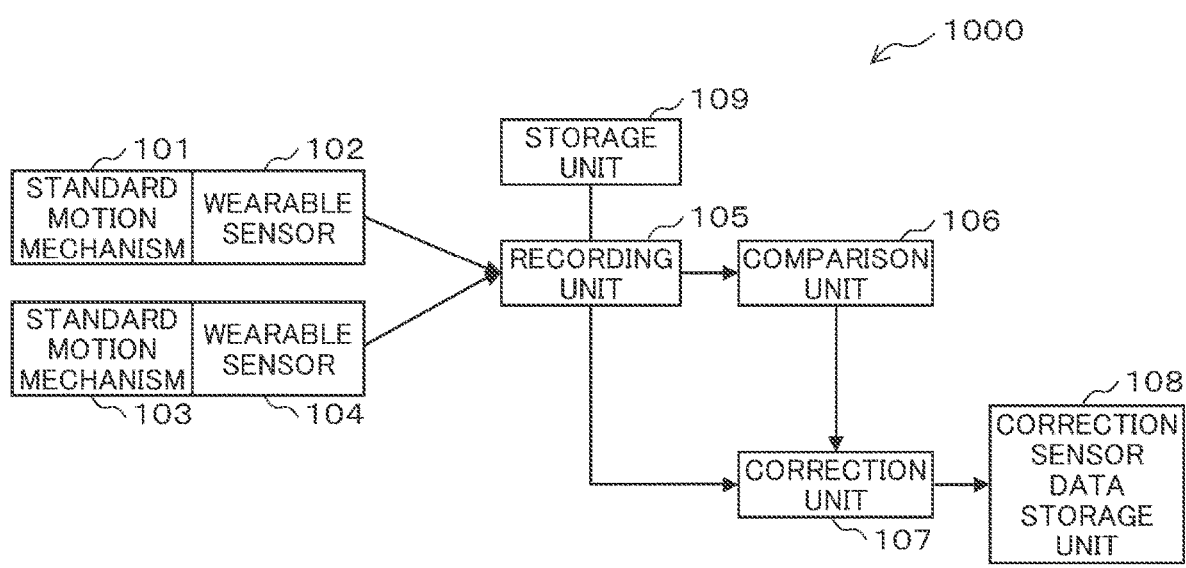
FIG. 1 is an example of a logical configuration for correcting an individual difference of sensing data of a wearable sensor.

An embodiment of the present invention will be described in detail by using the drawings. Here, the present invention is not interpreted by being limited to the contents of the following embodiment. It will be easily understood by a person skilled in the art that a specific configuration can be changed within a range not departing from the spirit or the gist of the present invention.

In the configuration of the present invention described below, the same reference numerals are commonly used in the same portions or portions having similar functions in different drawings, and the repeated description may be omitted.

Herein, notations such as "first", "second", and "third" are applied in order to identify constituents, and do not necessarily limit the number or the order. In addition, numbers for identifying constituents are used for each context, and numbers used in one context do not necessarily indicate the same constituents in another context. In addition, a constituent identified by a certain number may have the function of a constituent that is identified by another number.

The position, the size, the shape, the range, and the like of each configuration illustrated in the drawings or the like may be different from the actual position, the actual size, the actual shape, the actual range, and the like, in order to facilitate understanding of the present invention. For this reason, the present invention is not necessarily limited to the position, the size, the shape, the range, and the like illustrated in the drawings or the like.

EXAMPLE

FIG. 1 illustrates a configuration example of correcting an individual difference of sensing data of a wearable sensor of this example. As illustrated in FIG. 1, a sensor data correction system 1000 includes a wearable sensor 102, a wearable sensor 104, a recording unit 105, a comparison unit 106, a correction unit 107, a correction sensor data storage unit 108, and a storage unit 109. In FIG. 1, a standard motion mechanism 101 is mounted on the wearable sensor 102, and a standard motion mechanism 103 is mounted on the wearable sensor 104. In addition, in FIG. 1, the recording unit 105, the comparison unit 106, the correction unit 107, the correction sensor data storage unit 108, and the storage unit 109 are provided in a wearable device such as a glove including the wearable sensor 102 (or the wearable sensor 104).

The standard motion mechanism 101 is an instrument or a device on which the wearable sensor can be mounted. The standard motion mechanism 101 is capable of consistently performing a standard motion with constant force adjustment, a constant direction, and a constant speed. The standard motion mechanism 101 performs the standard motion in a state where the wearable sensor 102 is mounted. In a case where the standard motion is performed, the wearable sensor 102 transmits sensor data that is sensed by the standard motion to the recording unit 105 to be stored.

The standard motion mechanism 103 is the same instrument or device as the standard motion mechanism 101. The motion of the mechanism is the same as that of the standard motion mechanism 101, and thus, here, the description thereof will be omitted. Note that, in FIG. 1, it is illustrated that the standard motion mechanism 101 and the standard motion mechanism 103 are physically different from each other, but the standard motion mechanism 101 and the standard motion mechanism 103 may be physically one device or instrument.

The recording unit 105 records each of the sensor data items received from the wearable sensor 102 and the wearable sensor 104 in the storage unit 109, and outputs the recorded sensor data items to the comparison unit 106. The comparison unit 106 compares the sensor data items received from the recording unit 105, and outputs data indicating a difference between the sensor data items to the correction unit 107. The motion of the wearable sensor 102 and the wearable sensor 104 is consistently constant, and thus, it is possible to extract individual difference properties of the wearable sensor 102 and the wearable sensor 104 by calculating the difference between the sensor data items sensed by the wearable sensor 102 and the wearable sensor 104. The individual difference properties may be information indicating a difference in individual properties that are the properties of each of the wearable sensors, obtained from the sensor data items sensed by each of the wearable sensors.

The correction unit 107 corrects motion data of the wearable sensor 102 and the wearable sensor 104 that is recorded in the storage unit 109 by the recording unit 105, on the basis of the individual difference properties of the wearable sensor 102 and the wearable sensor 104 that are extracted by the comparison unit 106. The correction unit 107 records the corrected data in the correction sensor data storage unit 108. In FIG. 1, the correction sensor data storage unit 108 and the storage unit 109 are illustrated as different storage media or different storage devices, but may be configured as one storage unit.

Figure 2:
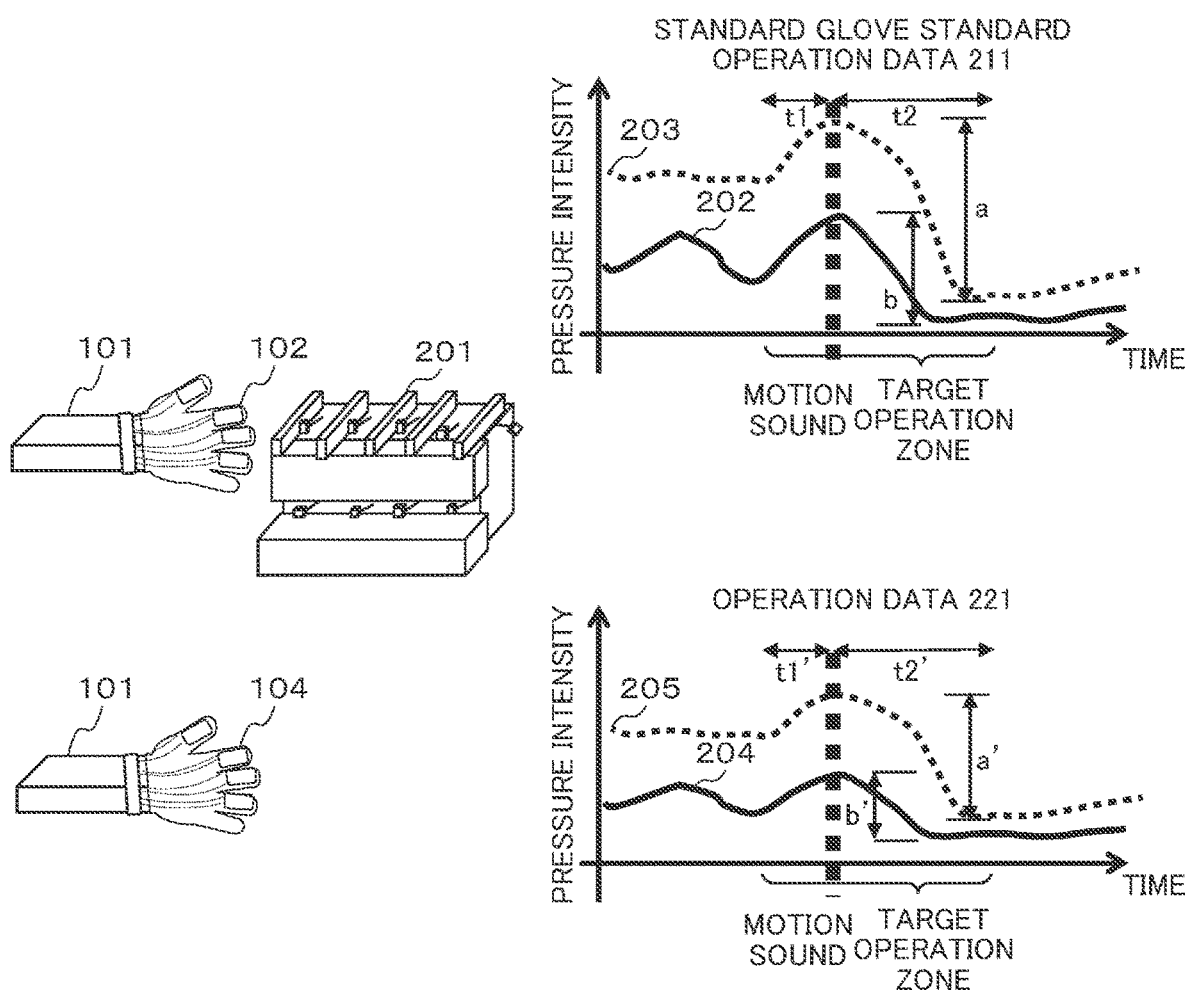
FIG. 2 is an example of a mode for correcting the individual difference of the wearable sensor.

FIG. 2 illustrates an example of a mode for correcting an individual difference of the wearable sensor. In FIG. 2, a case where the wearable sensor 102 is mounted on the standard motion mechanism 101 illustrated in FIG. 1 is exemplified. The wearable sensor 102 is a standard wearable sensor that is a reference for correction. The value of the sensor data that is acquired by another wearable sensor 104 mounted on the standard motion mechanism 101 illustrated in FIG. 1 is corrected on the basis of the value of the sensor data that is acquired by the wearable sensor 102.

The wearable sensor 102 is mounted on the standard motion mechanism 101, and then, the standard motion mechanism 101 performs the standard motion with respect to an instrument 201. The wearable sensor 102 transmits the sensor data at this time to the recording unit 105, as standard glove standard operation data 211, and the recording unit 105 records the standard glove standard operation data 211 in the storage unit 109.

The standard glove standard operation data 211, for example, includes data that can be sensed by the wearable sensor 102, such as pressure sensor data. Examples of the pressure sensor data include pressure data 202 that is sensed by the first finger, pressure data 203 that is sensed by the second finger, and the like. Obviously, examples of the pressure sensor data may include pressure data that is sensed by the third finger, the fourth finger, or the fifth finger. A time change of the pressure data 202 and the pressure data 203 can be notated as a graph. Such a graph is generated by the recording unit 105, and graph data thereof is recorded in the storage unit 109.

In this system, a motion sound is utilized in order to specify a time zone in which a target motion is performed. The wearable sensor 102 is mounted on the standard motion mechanism 101, and the standard motion is performed with respect to the instrument 201. A motion sound generated at this time is sensed by the wearable sensor 102, and the recording unit 105 extracts a time zone before and after the motion sound is sensed, as a target operation zone. The recording unit 105 defines the start and the end of the target operation zone as a start time t1 at which the increase of the pressure graph is started and an end time t2 at which the decrease of the pressure graph is ended. In a time range of the start time t1 to the end time t2, the recording unit 105 obtains the value of a difference a between a maximum value and a minimum value of the pressure data 203 that is sensed by the second finger and the value of a difference b between a maximum value and a minimum value of the pressure data 202 that is sensed by the first finger.

Similarly, the wearable sensor 104 is mounted on the standard motion mechanism 101, and then, the standard motion mechanism 101 performs the standard motion with respect to the instrument 201. The wearable sensor 104 transmits the sensor data at this time to the recording unit 105, as operation data 221, and the recording unit 105 records the operation data 221 in the storage unit 109.

The operation data 221, for example, includes data that can be sensed by the wearable sensor 102, such as the pressure sensor data. Examples of the pressure sensor data include pressure data 204 that is sensed by the first finger, pressure data 205 that is sensed by the second finger, and the like. Obviously, examples of the pressure sensor data may include pressure data that is sensed by the third finger, the fourth finger, or the fifth finger. A time change of the pressure data 204 and the pressure data 205 can be notated as a graph. Such a graph is generated by the recording unit 105, and graph data thereof is recorded in the storage unit 109.

As with the case of the standard glove standard operation data 211, the recording unit 105 defines the start and the end of the target operation zone as a start time t1' at which the increase of the pressure graph is started and an end time t2' at which the decrease of the pressure graph is ended. In a time range of the start time t1' to the end time t2', the recording unit 105 obtains the value of a difference a between a maximum value and a minimum value of the pressure data 205 that is sensed by the second finger and the value of a difference b' between a maximum value and a minimum value of the pressure data 204 that is sensed by the first finger.

Accordingly, the comparison unit 106 is capable of obtaining a ratio of the difference between the maximum value and the minimum value of the standard glove standard operation data 211 to the difference between the maximum value and the minimum value of the operation data 221, such as a/a' or b/b'. The correction unit 107, for example, multiplies the pressure data 205 of the second finger that is acquired as the operation data 221 by a/a', by using the ratio that is calculated by the comparison unit 106. In addition, the correction unit 107 multiplies the pressure data 204 of the first finger by b/b'. Accordingly, the value of the operation data 221 can be corrected as a value close to standard operation data.

As described above, the comparison unit 106 that is a determination unit calculates the properties of a first wearable sensor by using first sensor data that is sensor data in a operation zone of the first wearable sensor on which the standard motion mechanism 101 is mounted, and calculates the properties of a second wearable sensor by using second sensor data in an operation zone of the second wearable sensor in a zone corresponding to the operation zone, and the correction unit 107 performs the correction, on the basis of a relationship calculated by the determination unit from the properties of the wearable sensor 102 that is the first wearable sensor and the properties of the wearable sensor 104 that is the second wearable sensor. Note that, here, a correction method is an example, and it is obviously possible to perform the correction by using a general statistical value.

As described above, the individual properties of the wearable sensor can be corrected on the basis of the standard wearable sensor. That is, the comparison unit 106 that is the determination unit calculates a relationship between the first sensor data sensed by the wearable sensor 102 that is the first wearable sensor provided with the standard motion mechanism 101 for performing the standard motion of the wearable sensor, and the second sensor data sensed by the wearable sensor 104 that is the second wearable sensor provided with the standard motion mechanism 101, and the correction unit 107 corrects the first sensor data, on the basis of the relationship that is calculated by the determination unit, and thus, it is possible to accurately correct the individual properties of the wearable sensor. Note that, in this example, the first sensor data is corrected by using the relationship, the second sensor data may be corrected but by using the relationship.

Figure 3:
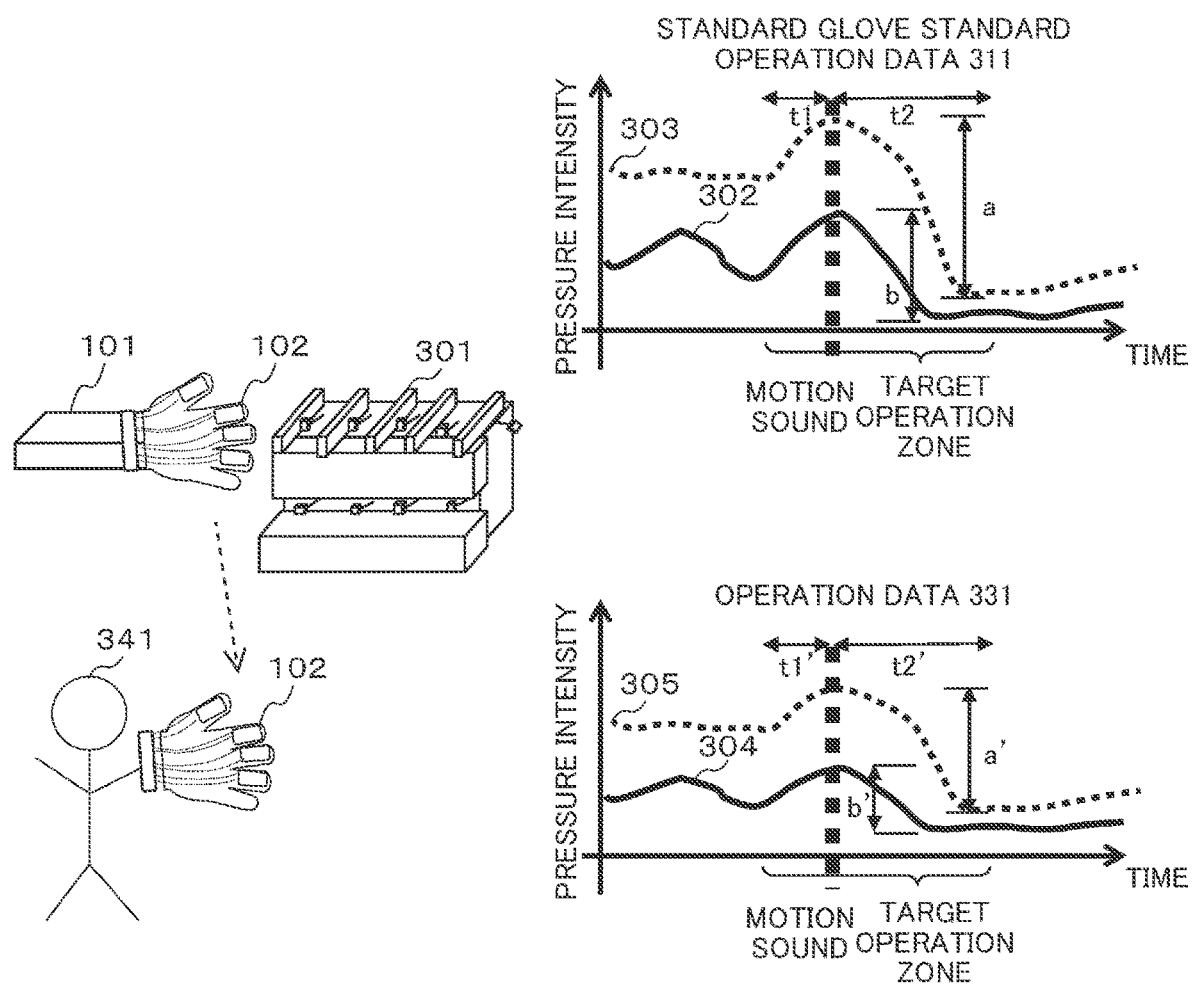
FIG. 3 is an example of a mode for correcting a personal difference of each person wearing the wearable sensor.

FIG. 3 illustrates an example of a mode for correcting a personal difference of each person wearing the wearable sensor. In FIG. 3, a case where the wearable sensor 102 is mounted on the standard motion mechanism 101 illustrated in FIG. 1 is exemplified. The wearable sensor 102 that is worn by an operator 341 is the same sensor as the wearable sensor 102 that is mounted on the standard motion mechanism 101.

The wearable sensor 102 is mounted on the standard motion mechanism 101, and then, the standard motion mechanism 101 performs the standard motion with respect to an instrument 301. The wearable sensor 102 transmits sensor data at this time to the recording unit 105 as standard operation data, and the recording unit 105 records standard glove standard operation data 311 in the storage unit 109.

The standard glove standard operation data 311, for example, includes data that can be sensed by the wearable sensor 102, such as the pressure sensor data. Examples of the pressure sensor data include pressure data 302 that is sensed by the first finger, pressure data 303 that is sensed by the second finger, and the like. Obviously, examples of the pressure sensor data may include pressure data that is sensed by the third finger, the fourth finger, or the fifth finger. A time change of the pressure data 320 and the pressure data 303 can be notated as a graph. Such a graph is generated by the recording unit 105, and graph data thereof is recorded in the storage unit 109.

In this system, the motion sound is utilized in order to specify the time zone in which the target motion is performed. The wearable sensor 102 is mounted on the standard motion mechanism 101, and the standard motion is performed with respect to the instrument 301. A motion sound generated at this time is sensed by the wearable sensor 102, and the recording unit 105 extracts the time zone before and after the motion sound is sensed, as the target operation zone. The recording unit 105 defines the start and the end of the target operation zone as the start time t1 at which the increase of the pressure graph is started and the end time t2 at which the decrease of the pressure graph is ended. In the time range of the start time t1 to the end time t2, the recording unit 105 obtains the value of a difference a between a maximum value and a minimum value of the pressure data 303 that is sensed by the second finger and the value of a difference b between a maximum value and a minimum value of the pressure data 302 that is sensed by the first finger.

Similarly, the wearable sensor 102 is worn by the operator 341 as with the sensor that is mounted on the standard motion mechanism 101, and then, the operator 341 performs the standard motion with respect to the instrument 301. The wearable sensor 102 transmits the sensor data at this time to the recording unit 105, as operation data 331, and the recording unit 105 records the operation data 331 in the storage unit 109.

The operation data 331, for example, includes data that can be sensed by the wearable sensor 102, such as the pressure sensor data. Examples of the pressure sensor data include pressure data 304 that is sensed by the first finger, pressure data 305 that is sensed by the second finger, and the like. Obviously, examples of the pressure sensor data may include pressure data that is sensed by the third finger, the fourth finger, or the fifth finger. A time change of the pressure data 304 and the pressure data 305 can be notated as a graph. Such a graph is generated by the recording unit 105, and graph data thereof is recorded in the storage unit 109.

As with the case of the standard glove standard operation data 311, the recording unit 105 defines the start and the end of the target operation zone as the start time t1' at which the increase of the pressure graph is started and the end time t2' at which the decrease of the pressure graph is ended. In the time zone of the start time t1' to the end time t2', the recording unit 105 obtains the value of a difference a between a maximum value and a minimum value of the pressure data 305 that is sensed by the second finger and the value of a difference b' between a maximum value and a minimum value of the pressure data 304 that is sensed by the first finger.

Accordingly, as with the description of FIG. 2, the comparison unit 106 is capable of obtaining a ratio of the difference between the maximum value and the minimum value of the standard glove standard operation data 311 to the difference between the maximum value and the minimum value of the operation data 331, such as a/a' or b/b'. The correction unit 107, for example, multiplies the pressure data 305 of the second finger that is acquired as the operation data 331 by a/a', by using the ratio that is calculated by the comparison unit 106. In addition, the correction unit 107 multiplies the pressure data of the first finger by b/b'. Accordingly, the value of the operation data 331 can be corrected as a value close to the standard operation data.

As described above, the comparison unit 106 that is the determination unit calculates the properties of the operator by using the sensor data in the operation zone of the wearable sensor 102, and calculates the properties standard motion mechanism 101 by using the standard sensor data in the zone corresponding to the operation zone, and the correction unit 107 performs the correction, on the basis of a relationship calculated by the determination unit from the properties of the operator wearing the wearable sensor 102 and the properties of the standard motion mechanism 101 provided with the wearable sensor 102. Note that, here, a correction method is an example, and it is obviously possible to perform the correction by using a general statistical value.

As described above, personal properties of the operator 341 can be corrected on the basis of the standard motion mechanism 101. The personal properties are physical characteristics of an individual hand such as the size of the hand or the length of the finger, and motional characteristics of the personal hand such as the habit of a bending mode and a gripping mode of the finger. The reflection of the personal properties on the data can be corrected. That is, the comparison unit 106 that is the determination unit calculates a relationship between the standard sensor data that is sensed by the wearable sensor 102 provided with the standard motion mechanism 101 for performing the standard motion of the wearable sensor and the sensor data that is sensed by the wearable sensor 102 worn by the operator, and the correction unit 107 corrects the sensor data, on the basis of the relationship that is calculated by the determination unit, and thus, it is possible to accurately correct the personal properties of the operator. Note that, in this example, the sensor data is corrected by using the relationship, but the standard sensor data may be corrected by using the relationship.

FIG. 4 illustrates an example of a mode for correcting the sensor data of the wearable sensor subjected to an aging variation. An operator 441 wears the wearable sensor 102, and grips a load cell 401. The load cell 401 senses the pressure that is applied to itself and outputs the value thereof.

The operator 441 performs the standard motion with respect to the load cell 401. The wearable sensor 102 transmits the sensor data at this time to the recording unit 105, as operation data 431, and the recording unit 105 records the storage unit 109 in the operation data 431. In addition, the load cell 401 transmits pressure data that is sensed to the recording unit 105, as load cell operation data 411, and the recording unit 105 records the load cell operation data 411 in the storage unit 109.

The load cell operation data 411, for example, includes data that can be sensed by the wearable sensor 102, such as the pressure sensor data. Examples of the pressure sensor data include pressure data 402 that is sensed by the first finger, pressure data 403 that is sensed by the second finger, and the like. Obviously, examples of the pressure sensor data may include pressure data that is sensed by the third finger, the fourth finger, or the fifth finger. A time change of the pressure data 403 and the pressure data 402 can be notated as a graph. The graph is generated by the recording unit 105, and graph data thereof is recorded in the storage unit 109.

In this system, the motion sound is utilized in order to specify the time zone in which the target motion is performed. The operator 441 wears the wearable sensor 102, and performs a motion with respect to the load cell 401. A motion sound generated at this time is sensed by the wearable sensor 102, and the recording unit 105 extracts the time zone before and after the motion sound is sensed, as the target operation zone. The recording unit 105 defines the start and the end of the target operation zone as the start time t1 at which the increase of the pressure graph is started and the end time t2 at which the decrease of the pressure graph is ended. In the time range of the start time t1 to the end time t2, the recording unit 105 obtains the value of a difference a between a maximum value and a minimum value of the pressure data 403 that is sensed by the load cell 401 by receiving a pressure from the second finger and the value of a difference b between a maximum value and a minimum value of the pressure data 402 that is sensed by the load cell 401 by receiving a pressure from the first finger.

Similarly, the operation data 431, for example, includes data that can be sensed by the wearable sensor 102, such as the pressure sensor data. Examples of the pressure sensor data include pressure data 404 that is sensed by the first finger, pressure data 405 that is sensed by the second finger, and the like. Obviously, examples of the pressure sensor data may include pressure data that is sensed by the third finger, the fourth finger, or the fifth finger. A time change of the pressure data 404 and the pressure data 405 can be notated as a graph. Such a graph is generated by the recording unit 105, and graph data thereof is recorded in the storage unit 109.

As with the case of the load cell operation data 411, the recording unit 105 defines the start and the end of the target operation zone as the start time t1' at which the increase of the pressure graph is started and end time t2' at which the decrease of the pressure graph is ended. In the time range of the start time t1' to the end time t2', the recording unit 105 obtains the value of a difference a' between a maximum value and a minimum value of the pressure data 405 that is sensed by the second finger and the value of a difference b' between a maximum value and a minimum value of the pressure data 404 that is sensed by the first finger.

Accordingly, as with the description of FIG. 2, the comparison unit 106 is capable of obtaining a ratio of the difference between the maximum value and the minimum value of the load cell operation data 411 to the difference between the maximum value and the minimum value of the operation data 431. The correction unit 107, for example, multiplies the pressure data of the second finger by a/a', by using the ratio that is calculated by the comparison unit 106, with respect to the pressure data that is acquired as the operation data 431. In addition, the correction unit 107 multiplies the pressure data of the first finger by b/b'. Accordingly, the value of the operation data 431 can be corrected as a value close to the load cell operation data. Here, a correction method is an example, and it is obviously possible to perform the correction by using a general statistical value.

As described above, individual properties of the wearable sensor 102 subjected to a time degradation can be corrected on the basis of the load cell 401. That is, the load cell 401 senses a pressure that is received, the comparison unit 106 that is the determination unit calculates a relationship between first sensor data that is sensed by the wearable sensor 102 worn by the operator and second sensor data in which the load cell 401 senses a pressure from the wearable sensor 102, and the correction unit 107 corrects the first sensor data that is sensed by the wearable sensor 102, on the basis of the relationship that is calculated by the determination unit, and thus, it is possible to accurately correct the individual properties of the wearable sensor subjected to the time degradation. Note that, in this example, the first sensor data is corrected by using the relationship, but the second sensor data may be corrected by using the relationship.

Figure 5:
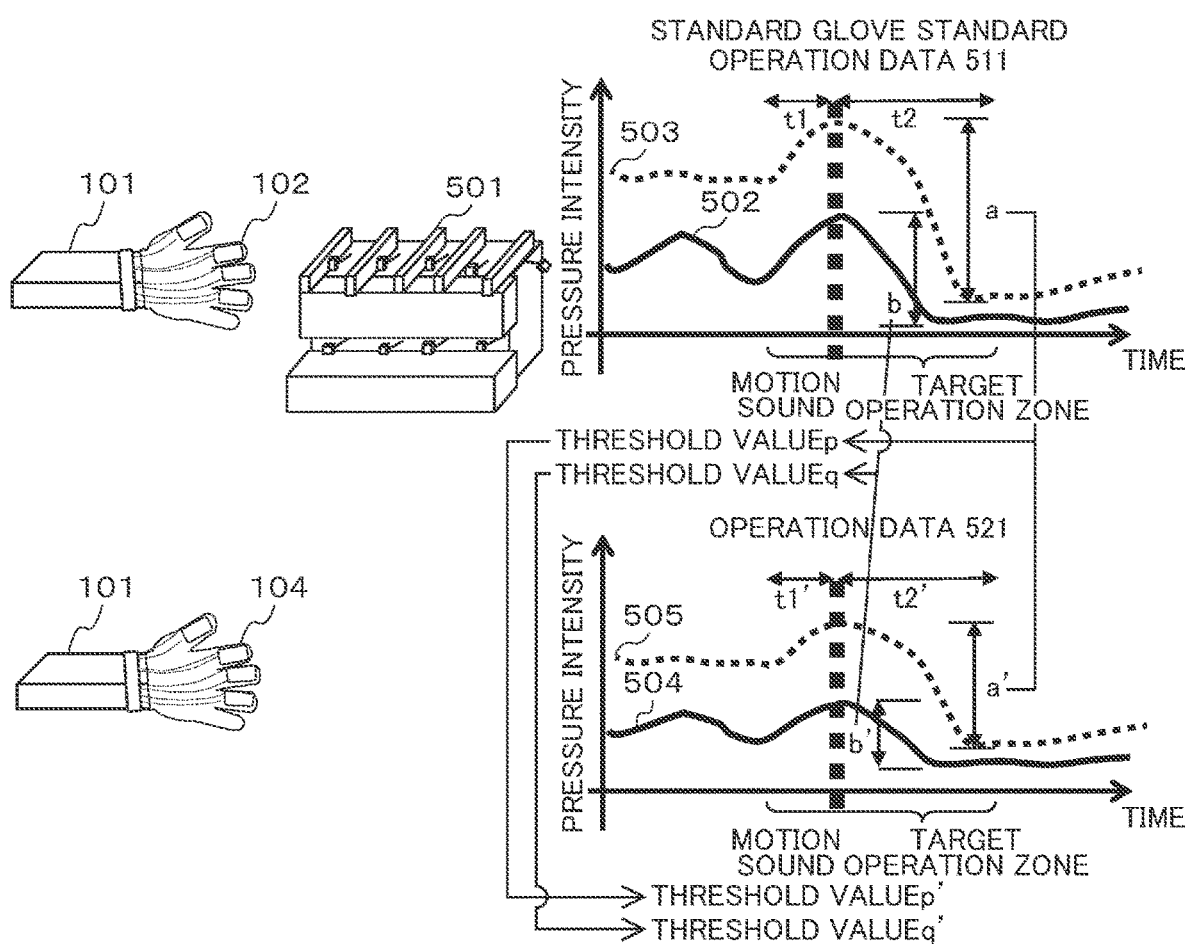
FIG. 5 is an example of a mode for adjusting a threshold value in motion determination with respect to the individual difference of the wearable sensor.

FIG. 5 illustrates an example of a mode for adjusting a threshold value with respect to the individual difference of the wearable sensor, in motion determination but not in data correction. In FIG. 5, a case where the wearable sensor 102 is mounted on the standard motion mechanism 101 illustrated in FIG. 1 is exemplified. The wearable sensor 102 is a standard wearable sensor that is a reference for the threshold value in the motion determination. In the value of the sensor data that is acquired by another wearable sensor 104, the threshold value of the motion determination is set on the basis of the value of the sensor data that is acquired by the wearable sensor 102.

The wearable sensor 102 is mounted on the standard motion mechanism 101, and then, the standard motion mechanism 101 performs the standard motion with respect to an instrument 501. The wearable sensor 102 transmits the sensor data at this time to the recording unit 105, as the standard glove standard operation data, and the recording unit 105 records standard glove standard operation data 511 in the storage unit 109.

The standard glove standard operation data 511, for example, includes data that can be sensed by the wearable sensor 102, such as the pressure sensor data. Examples of the pressure sensor data include pressure data 502 that is sensed by the first finger, pressure data 503 that is sensed by the second finger, and the like. Obviously, examples of the pressure sensor data may include pressure data that is sensed by the third finger, the fourth finger, or the fifth finger. A time change of the pressure data 502 and the pressure data 503 can be notated as a graph. Such a graph is generated by the recording unit 105, and graph data thereof is recorded in the storage unit 109.

In this system, the motion sound is utilized in order to specify the time zone in which the target motion is performed. The wearable sensor 102 is mounted on the standard motion mechanism 101, and the standard motion is performed with respect to the instrument 501. A motion sound generated at this time is sensed by the wearable sensor 102, and the recording unit 105 extracts the time zone before and after the motion sound is sensed, as the target operation zone. The recording unit 105 defines the start and the end of the target operation zone as the start time t1 at which the increase of the pressure graph is started and the end time t2 at which the decrease of the pressure graph is ended. In the time range of the start time t1 to the end time t2, the recording unit 105 obtains the value of a difference a between a maximum value and a minimum value of the pressure data 503 that is sensed by the second finger and the value of a difference b between a maximum value and a minimum value of the pressure data 502 that is sensed by the first finger.

Similarly, the wearable sensor 104 is mounted on the standard motion mechanism 101, and the standard motion mechanism 101 performs the standard motion with respect to the instrument 501. The wearable sensor 104 transmits the sensor data at this time to the recording unit 105, as operation data 521, and the recording unit 105 records the operation data 331 in the storage unit 109.

The operation data 521, for example, includes data that can be sensed by the wearable sensor 102, such as the pressure sensor data. Examples of the pressure sensor data include pressure data 504 that is sensed by the first finger, pressure data 505 that is sensed by the second finger, and the like. Obviously, examples of the pressure sensor data may include pressure data that is sensed by the third finger, the fourth finger, or the fifth finger. A time change of the pressure data 503 and the pressure data 504 can be notated as a graph. Such a graph is generated by the recording unit 105, and graph data thereof is recorded in the storage unit 109.

As with the case of the standard glove standard operation data 511, the recording unit 105 defines the start and the end of the target operation zone as the start time t1' at which the increase of the pressure graph is started and the end time t2' at which the decrease of the pressure graph is ended. In the time range of the start time t1' to the end time t2', the recording unit 105 obtains the value of a difference a between a maximum value and a minimum value of the pressure data 505 that is sensed by the second finger and the value of a difference b' between a maximum value and a minimum value of the pressure data 504 that is sensed by the first finger.

Accordingly, the comparison unit 106 is capable of obtaining a ratio of the difference between the maximum value and the minimum value of the standard glove standard operation data 511 to the difference between the maximum value and the minimum value of the operation data 521, such as a/a' or b/b'. As illustrated in FIG. 2, the correction unit 107 is also capable of adjusting the threshold value of the determination based on a change of the sensor data but not the data correction, by using the ratio that is calculated by the comparison unit 106.

Here, a determination threshold value will be described. The determination threshold value is a value for determining that a motion satisfying a certain condition is performed in the case of exceeding the value. The determination threshold value is a threshold value for determining the motion that is performed by the standard motion mechanism 101, in accordance with the size of the sensor data. The threshold value, for example, is stored in the storage unit 109.

The correction unit 107 sets a determination threshold value p' and a determination threshold value q' in the operation data 521 with respect to a determination threshold value p and a determination threshold value q in the standard glove standard operation data 511, on the basis of a/a' and b/b'. That is, the correction unit 107 sets each of the determination threshold values p' and q' to a product of the determination threshold value p and a/a' and a product of the determination threshold value q and b/b'. As described above, the correction unit 107 sets a determination threshold value for determining that a predetermined motion is performed by using the first wearable sensor or the second wearable sensor, on the basis of the properties of the first wearable sensor provided with the standard motion mechanism 101 and the properties of the second wearable sensor provided with the standard motion mechanism 101.

According to such setting, it is possible to set the threshold value of the motion determination with respect to acquired data of a wearable sensor 531, on the basis of individual properties of the wearable sensor 531, without performing the data correction. For example, in a case where a use frequency of an instrument sensing a load or a pressure, such as a load cell, is less than that of a wearable sensor that is worn by an operator, it is possible to sense the load or the pressure with a correct sensitivity even when years have elapsed. On the other hand, the wearable sensor is frequently worn by the operator, and thus, the sensitivity decreases as years have elapsed. For this reason, in a case where the same determination threshold value is set regardless of the elapsed years, it is not possible to perform correct determination by using the sensed sensor data. Therefore, as described above, the comparison unit 106 sets again the threshold value, in accordance with a decrease in the sensitivity, and thus, it is possible to accurately determine the motion by using the sensor data that is obtained from the wearable sensor.

Figure 6:
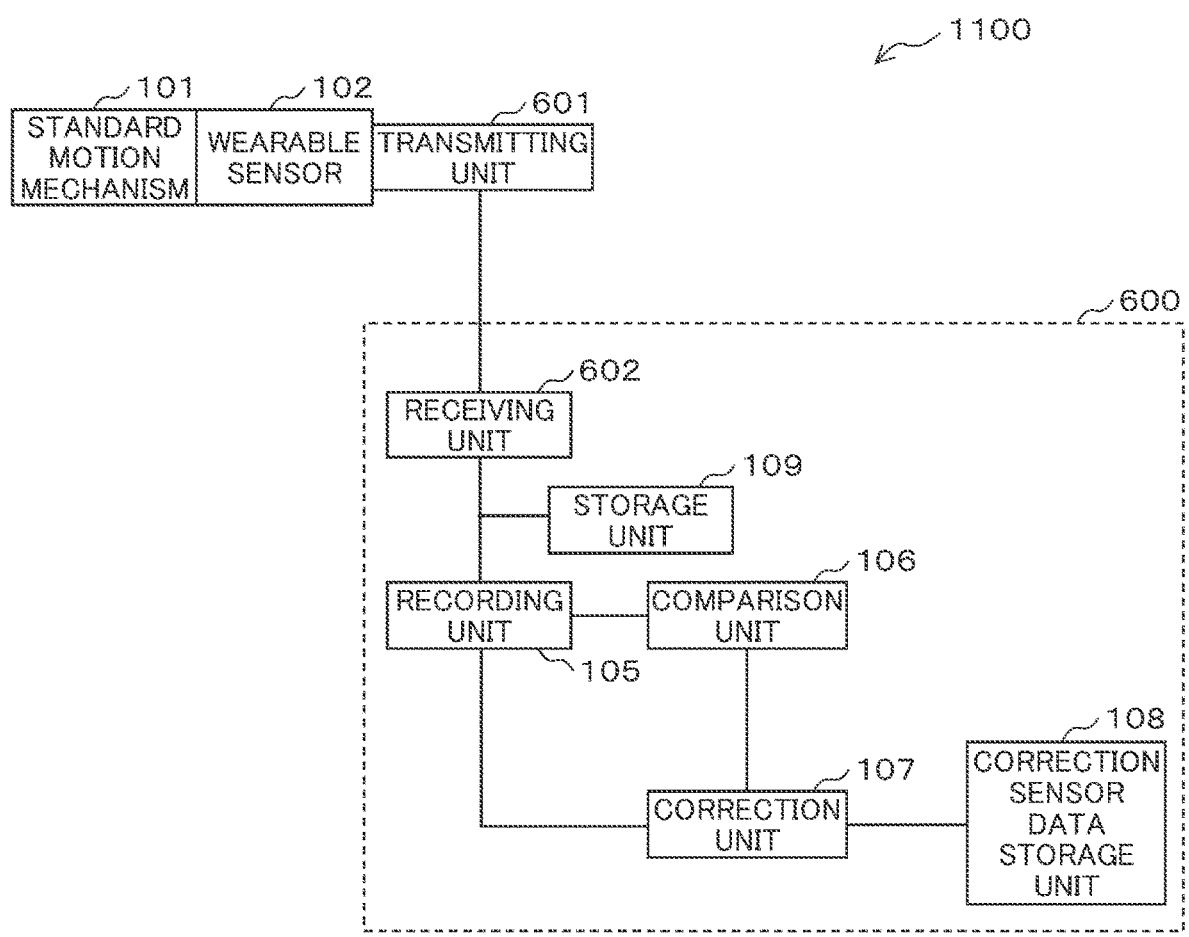
FIG. 6 is an example of a configuration in which a recording unit, a comparison unit, a correction unit, and a correction sensor data recording unit are provided outside the wearable sensor.

FIG. 6 is a diagram illustrating a configuration example of a sensor data correction system 1100 including the recording unit 105, the comparison unit 106, the correction unit 107, the correction sensor data storage unit 108, and the storage unit 109, in addition to the wearable device provided with the wearable sensor in the sensor data correction system 1000 illustrated in FIG. 1. In FIG. 6, each of the units is provided in an information processing device 600. For example, a transmitting unit 601 for communicating with the information processing device 600 such as a server computer through a network is provided in the wearable device provided with the wearable sensor 102. In addition, a receiving unit 602 for communicating with the wearable sensor 102 through a network is provided in the information processing device 600.

In FIG. 6, the wearable sensor 102 is mounted on the standard motion mechanism 101, and a transmitting unit 601 transmits sensor data that is acquired by the wearable sensor 102 to the receiving unit 602.

In a case where the receiving unit 602 receives the sensor data from the transmitting unit 601, the recording unit 105 records the same operation data as the operation data 331 in the storage unit 109. After that, the same processing as that of the case of FIG. 1 is performed.

In FIG. 6, the sensor data correction system 1100 includes a unit including the wearable sensor 102 that is the first wearable sensor or the wearable sensor 104 that is the second wearable sensor, the standard motion mechanism 101, and the transmitting unit 601 for transmitting the first sensor data sensed by the wearable sensor 102 that is the first wearable sensor provided with the standard motion mechanism 101 or the second sensor data sensed by the wearable sensor 104 that is the second wearable sensor provided with the standard motion mechanism 101, and the information processing device 600 including the receiving unit 602 for receiving the first sensor data or the second sensor data described above, the comparison unit 106 that is the determination unit, and the correction unit 107.

As described above, in the sensor data correction system 1100, the wearable device transmits the sensor data to the information processing device, and as with the case of FIG. 1, executes processing of correcting the information processing device sensor data, and thus, it is possible to make the configuration of the wearable device simple, and to suppress a load on the wearable device.

Figure 7:
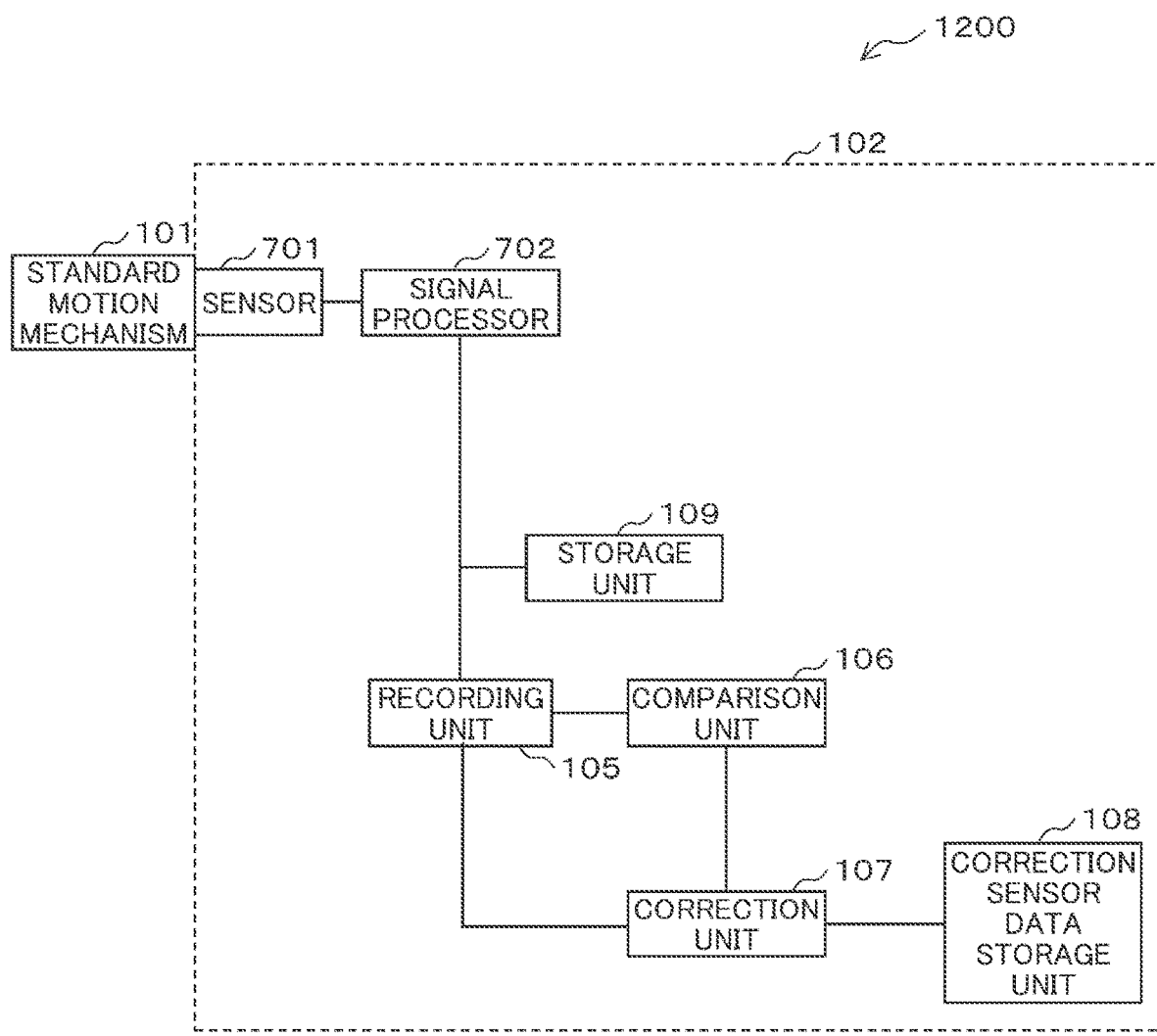
FIG. 7 is an example of a configuration in which a signal processor, a comparison unit, a correction unit, and a correction sensor data recording unit are provided in the wearable sensor.

FIG. 7 is a diagram illustrating a configuration example of a sensor data correction system 1200 in which the wearable sensor includes the recording unit 105, the comparison unit 106, the correction unit 107, the correction sensor data storage unit 108, and the storage unit 109, in the sensor data correction system 1000 illustrated in FIG. 1. In FIG. 7, each of the units is provided in the wearable sensor 102. The wearable sensor 102 includes a sensor 701 sensing a motion (for example, a load or a pressure) when the standard motion is performed from the standard motion mechanism 101 performing the standard motion, and a signal processor 702 converting the motion sensed by the sensor 701 into a data signal.

In FIG. 7, the wearable sensor 102 is mounted on the standard motion mechanism 101, and the signal processor 702 converts the motion sensed by the sensor 701 into the data signal, and outputs the data signal to the recording unit 105. In a case where the data signal is received from the signal processor 702, the recording unit 105 records the same operation data as the operation data 331 in the storage unit 109. After that, the same processing as that of the case of FIG. 1 is performed.

In FIG. 7, the sensor data correction system 1200 includes a sensor unit including the wearable sensor 102 that is the first wearable sensor or the wearable sensor 104 that is the second wearable sensor, the standard motion mechanism 101, the signal processor 702 converting the motion that is sensed by the first wearable sensor or the second wearable sensor described above into the data signal, the comparison unit 106 that is the determination unit calculating the relationship between the properties of the wearable sensor 102 that is the first wearable sensor described above and the properties of the wearable sensor 104 that is the second wearable sensor described above, by using the converted data signal, and the correction unit 107 performing the correction, on the basis of the relationship that is calculated by the determination unit described above.

Note that, in consideration of actual implementation, it is considered that the recording unit, the comparison unit, the correction unit, and the correction sensor data recording unit are more likely to be implemented in a high-order system in which processing performance or a record amount is easily increased, that is, the configuration of FIG. 6 is more likely to be implemented. However, in the case of an environment in which communication with respect to the high-order system is not capable of being performed or a case where the wearable sensor has high performance, as with the case of FIG. 1, it is possible to accurately correct the sensor data by adopting the configuration illustrated in FIG. 7.

Figure 8:
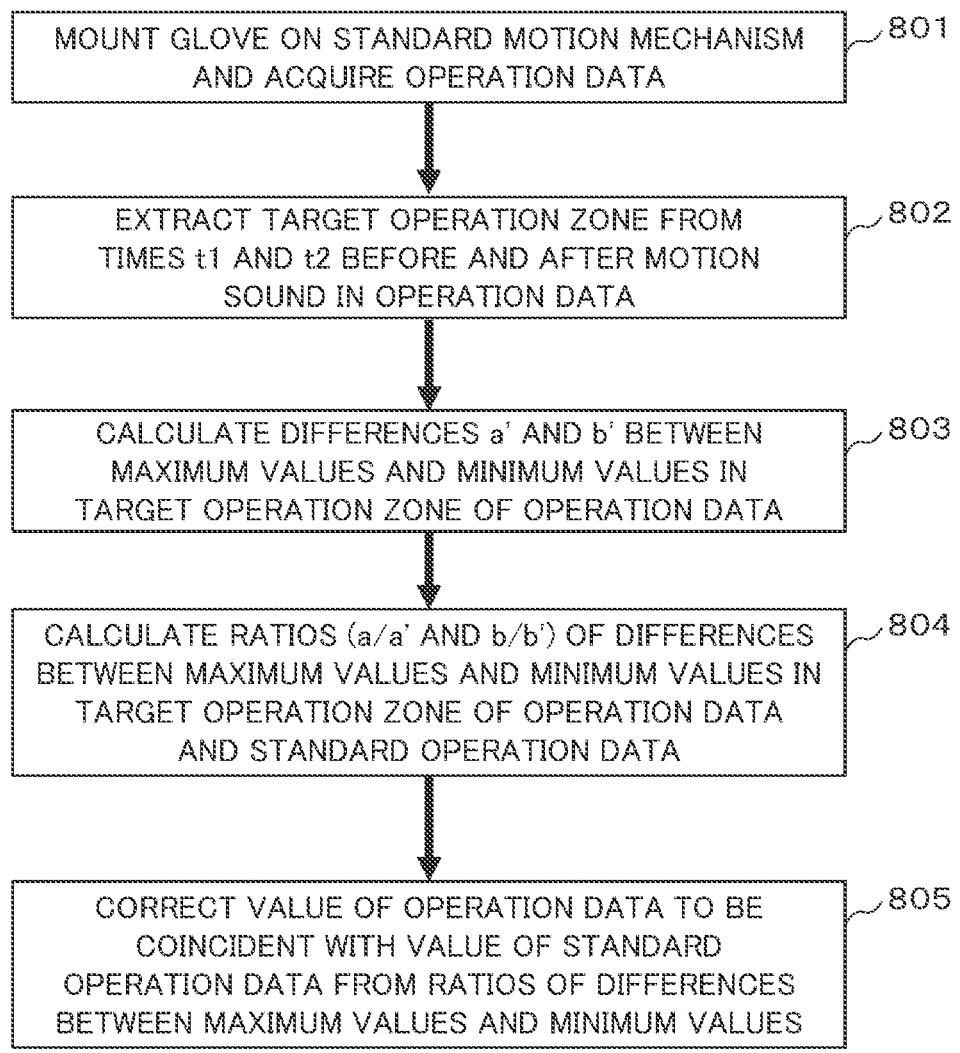
FIG. 8 is an example of a flowchart of correcting a wearable sensor individual difference.

FIG. 8 illustrates an example of a flowchart illustrating a processing procedure of processing for correcting the individual difference of the wearable sensor illustrated in FIG. 2 (individual difference correction processing). Hereinafter, the standard glove standard operation data 211, the value of the difference a between the maximum value and the minimum value of the pressure data 203 that is sensed by the second finger, and the value of the difference b between the maximum value and the minimum value of the pressure data 202 that is sensed by the first finger are stored in advance in the storage unit 109. Such data items can be acquired by performing the following processing.

In the individual difference correction processing, a glove that is the wearable device is mounted on the standard motion mechanism 101, and the operation data 221 is acquired by the wearable sensor 104 provided in the glove (Step 801). After that, the recording unit 105 extracts the time zone between the start time t1 and the end time t2, before and after the motion sound is sensed, from the operation data 221, as the target operation zone (Step 802).

The comparison unit 106 calculates the difference a' between the maximum value and the minimum value of the pressure data 205 that is sensed by the second finger and the difference b' between the maximum value and the minimum value of the pressure data 204 that is sensed by the first finger, in the target operation zone of the operation data 221 (Step 803). The comparison unit 106 calculates the ratios (a/a' and b/b') of such values, and the difference a between the maximum value and the minimum value of the pressure data 203 that is sensed by the second finger and the difference b between the maximum value and the minimum value of the pressure data 202 that is sensed by the first finger, in the target operation zone of the standard glove standard operation data 211 (Step 804), and the correction unit 107 corrects the value of the operation data 211 to be coincident with the value of the glove standard operation data 211 (Step 805). As described above, the individual difference correction processing is executed, and thus, it is possible to correct the individual properties of the wearable sensor, on the basis of the standard wearable sensor.

Figure 9:
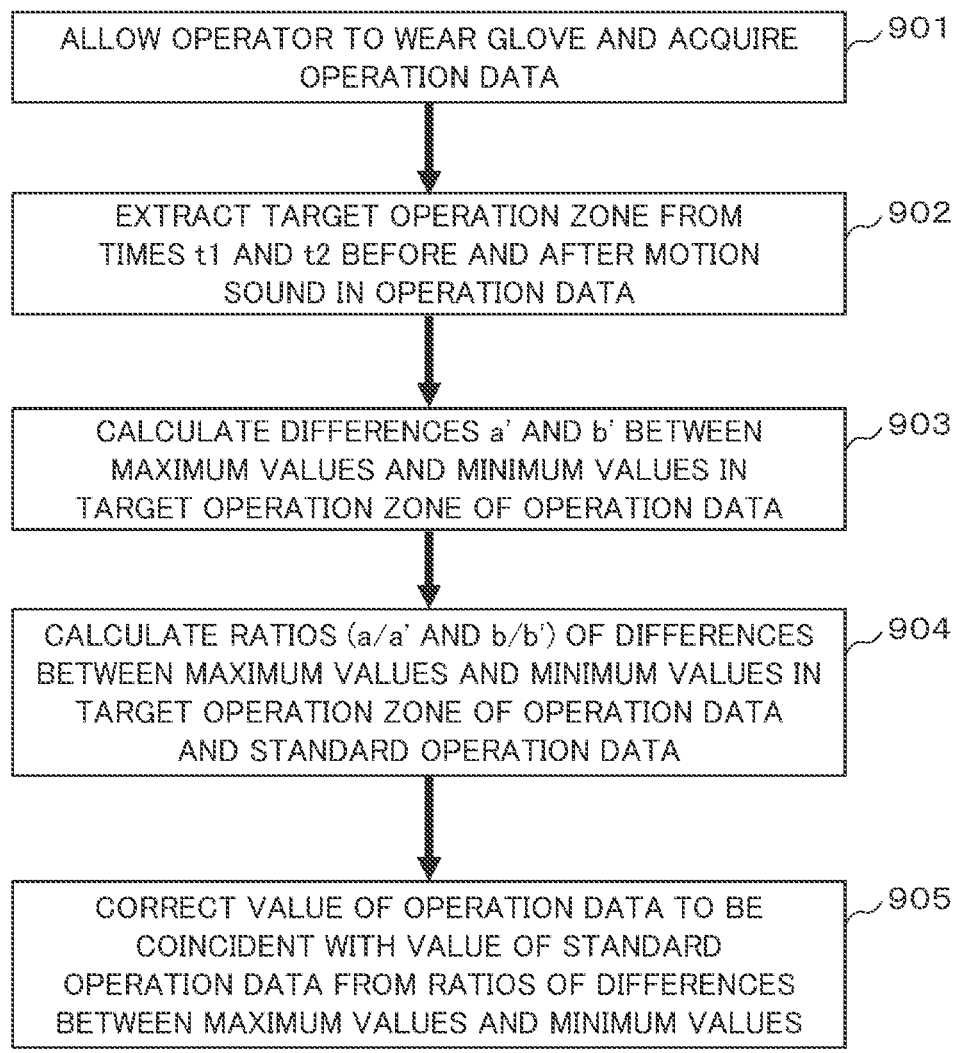
FIG. 9 is an example of a flowchart of correcting personal properties of a person.

FIG. 9 illustrates an example of a flowchart illustrating a processing procedure of processing for correcting a personal difference of each person wearing the wearable sensor illustrated in FIG. 3 (personal difference correction processing). Hereinafter, the standard operation data 311, the value of the difference a between the maximum value and the minimum value of the pressure data 303 that is sensed by the second finger, and the value of the difference b between the maximum value and the minimum value of the pressure data 302 that is sensed by the first finger are stored in advance in the storage unit 109. Such data items can be acquired by performing the following processing.

In the personal difference correction processing, the glove that is the wearable device is worn by the operator 341, the operation data 331 is acquired by the wearable sensor 102 provided in the glove (Step 901). After that, the recording unit 105, the comparison unit 106, and the correction unit 197 execute the same processing as that of Step 802 to Step 805 in FIG. 8 (Step 902 to Step 905). As described above, the personal difference correction processing is executed, and thus, it is possible to correct the personal properties of the operator 341, on the basis of the standard motion mechanism 101.

FIG. 10 illustrates an example of a flowchart illustrating a processing procedure of processing for correcting an aging variation of the wearable sensor illustrated in FIG. 4 (aging variation correction processing). Hereinafter, the load cell operation data 411, the value of the difference a between the maximum value and the minimum value of the pressure data 403 that is sensed by the second finger, and the value of the difference b between the maximum value and the minimum value of the pressure data 402 that is sensed by the first finger are stored in advance in the storage unit 109. Such data items can be acquired by performing the following processing.

In the aging variation correction processing, the operator 441 wears the glove that is the wearable device and grips the load cell 401, the wearable sensor 102 transmits the operation data 431 to the recording unit 105, and the recording unit 105 acquires the operation data 431, and the load cell operation data 411 that is stored in advance in the storage unit 109 (Step 1001). After that, the comparison unit 106 calculates the ratios (a/a' and b/b') of the difference a between the maximum value and the minimum value of the pressure data 403 that is sensed by the second finger and the difference b between the maximum value and the minimum value of the pressure data 402 that is sensed by the first finger, in the operation zone of the load cell operation data 411, to the difference a' between the maximum value and the minimum value of the pressure data 405 that is sensed by the second finger and the difference b' between the maximum value and the minimum value of the pressure data 404 that is sensed by the first finger, in the operation zone of the operation data 431 (Step 1002). The correction unit 107 corrects the value of the operation data 431 to be coincident with the value of the load cell operation data 411 (Step 1003). As described above, the aging variation correction processing is executed, and thus, it is possible to correct the individual properties of the wearable sensor 102 subjected to the time degradation, on the basis of the load cell 401.

Figure 11:
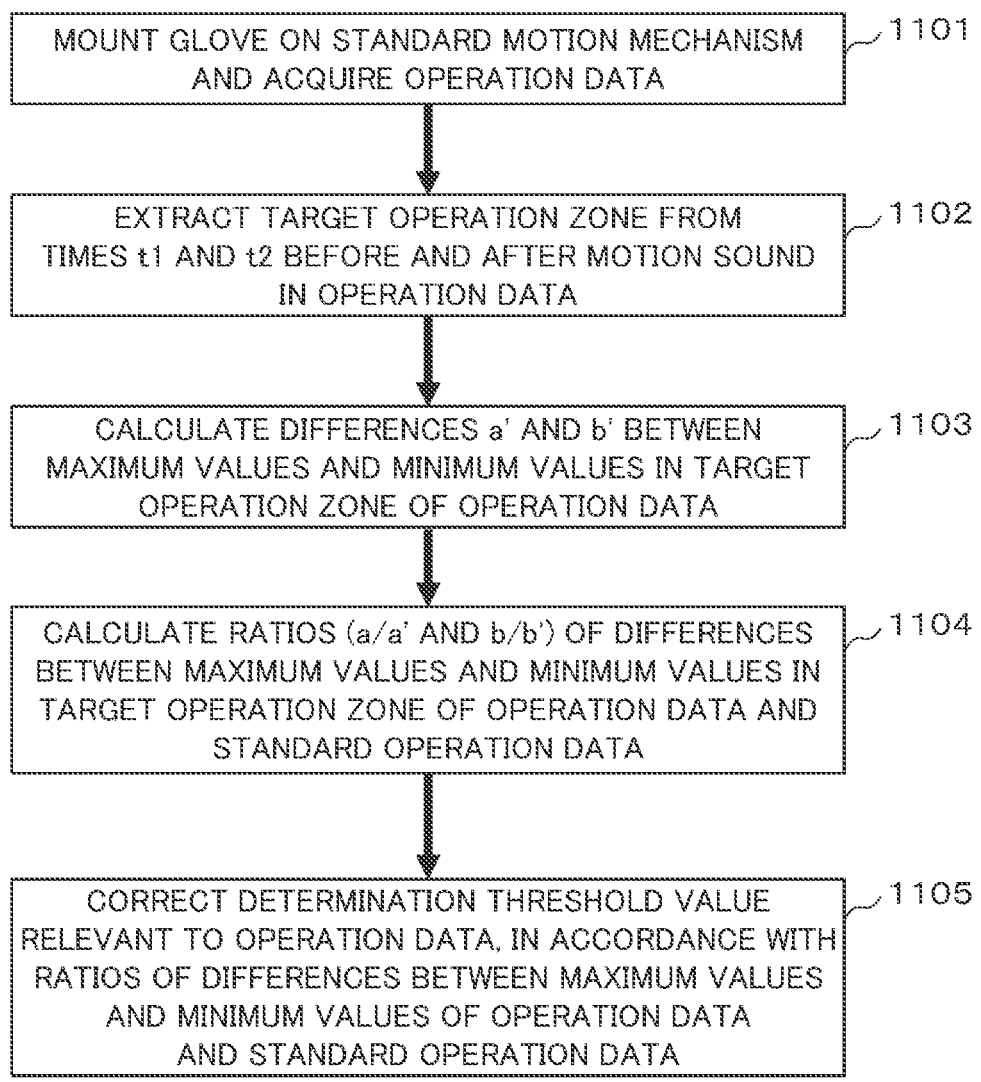
FIG. 11 is an example of a flowchart of adjusting a determination threshold value.

FIG. 11 illustrates an example of a flowchart illustrating a processing procedure of processing for adjusting the determination threshold value illustrated in FIG. 5 (determination threshold value adjustment processing). Hereinafter, as with the case of FIG. 8, the standard glove standard operation data 211, the value of the difference a between the maximum value and the minimum value of the pressure data 203 that is sensed by the second finger, and the value of the difference b between the maximum value and the minimum value of the pressure data 202 that is sensed by the first finger are stored in advance in the storage unit 109. Such data items can be acquired by performing the following processing.

In the determination threshold value adjustment processing, the wearable sensor 104, the recording unit 105, and the comparison unit 106 execute the same processing as that of Step 801 to Step 804 in FIG. 8 (Step 901 to Step 904). The processing of such steps is the same as that of FIG. 8, and thus, here, the description thereof will be omitted.

In a case where the ratios (a/a' and b/b') of the difference a between the maximum value and the minimum value of the pressure data 203 that is sensed by the second finger and the difference b between the maximum value and the minimum value of the pressure data 202 that is sensed by the first finger are calculated, the correction unit 107 corrects the determination threshold value, in accordance with the calculated ratios of the differences between the maximum values and the minimum values (Step 1105). As described above, the determination threshold value adjustment processing is executed, and thus, it is possible to set the threshold value of the motion determination, on the basis of the individual properties of the wearable sensor 531, without performing the data correction.

Figure 12:
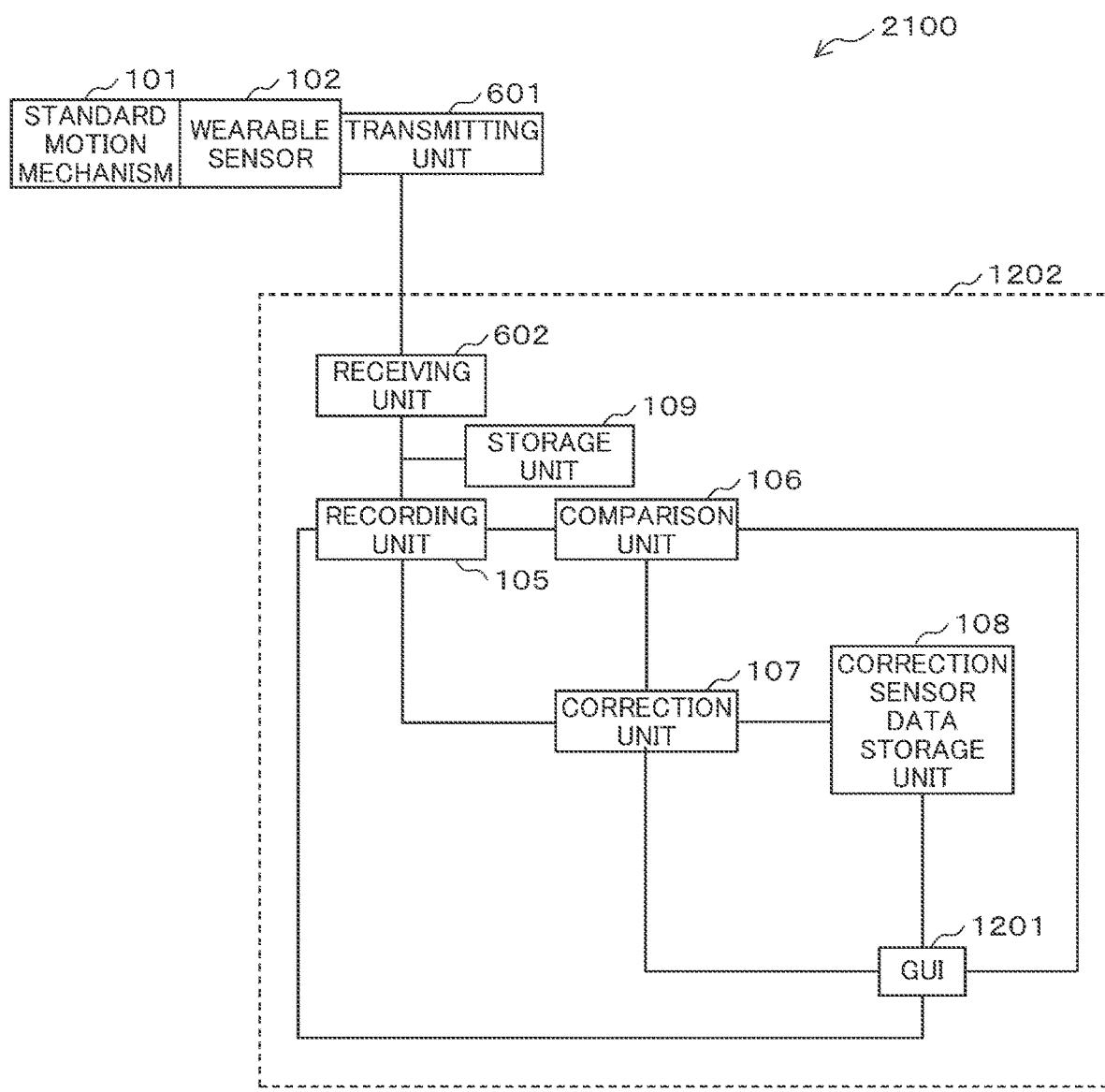
FIG. 12 is an example of a configuration in which a recording unit, a comparison unit, a correction unit, a correction sensor data recording unit, and a GUI are provided outside the wearable sensor.

FIG. 12 is a diagram illustrating a configuration example of a sensor data correction system 2100 including an information processing device 1202 in which a GUI (a display control unit) 1201 for the information processing device 600 to display information on a display device such as a display is provided in the sensor data correction system 1100 illustrated in FIG. 6. Each of the units other than the GUI 1201 in the sensor data correction system 2100 is identical to each of the units illustrated in FIG. 6, and thus, here, the description thereof will be omitted, and the GUI 1201 will be described.

Figure 15:
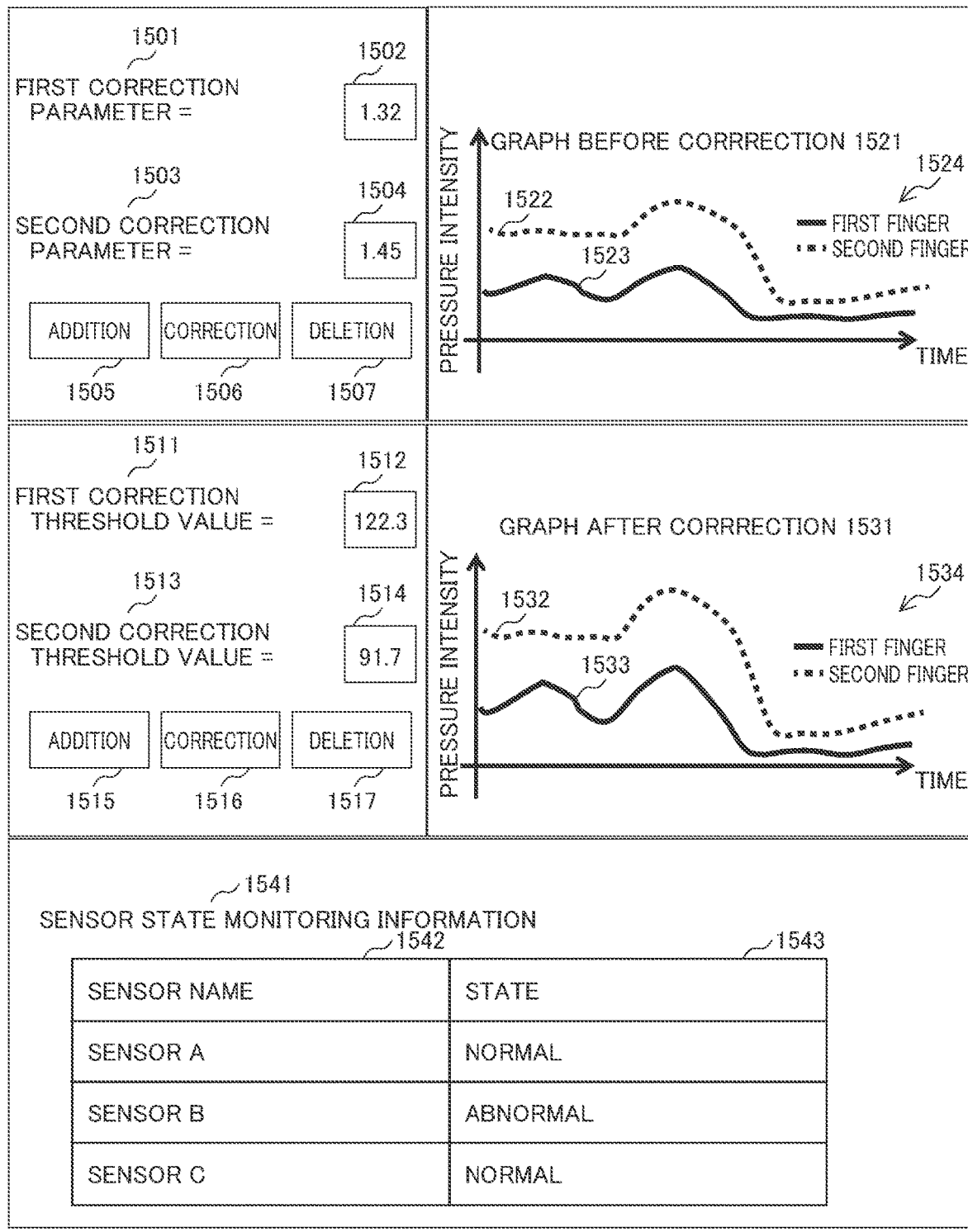
FIG. 15 is an example of a GUI that is capable of adding, deleting, and changing a conversion value or a threshold value used in correction, of displaying sensor data before and after the correction in a graph, or of displaying an alert in a case where the sensor is not in a correctable state.

FIG. 15 is a diagram illustrating an example of a screen that is displayed on the display device by the GUI 1210. The GUI 1201 visualizes and displays the sensor data recorded in the recording unit 105, a comparison result compared by the comparison unit 106, a correction result corrected by the correction unit 107, data after correction stored in the correction sensor data storage unit 108. In addition, the GUI 1201 displays a conversion value or a threshold value used in the correction in a form that can be added, deleted, or changed. Further, in a case where the wearable sensor is not in a correctable state, the GUI 1201 presents an alert.

FIG. 15 illustrates an example of the GUI that is capable of adding, deleting, or changing the conversion value or the threshold value used in the correction, of displaying the sensor data of the wearable sensor before and after the correction as a graph, or of displaying the alert in a case where the wearable sensor is not in the correctable state. Note that, in FIG. 15, a case where five windows are displayed on one display device is exemplified, but the windows may be displayed on display devices, respectively.

A first correction parameter 1501, for example, is a parameter indicating the ratio a/a' of the differences between the maximum values and the minimum values of the pressure data of the second finger in the description of FIG. 2. In FIG. 15, it is illustrated that "1.32" is set in a setting field 1502 of the value.

A second correction parameter 1503, for example, is a parameter indicating the ratio b/b' of the differences between the maximum values and the minimum values of the pressure data of the first finger in the description of FIG. 2. In FIG. 15, it is illustrated that "1.45" is set in a setting field 1504 of the value.

Each of the correction parameters can be increased by manipulating an addition button 1505. For example, the addition button 1505 is pressed down, and thus, the GUI 1201 newly displays a row of a third correction parameter.

Each of the correction parameters can be corrected by manipulating a correction button 1506. For example, the correction button 1506 is pressed down, and thus, the GUI 1201 sets the setting field 1502 of the first correction parameter 1501 or the setting field 1504 of the second correction parameter 1503 to be in a state where input is available, and receives the change of such setting values.

Further, the correction parameter can be deleted by manipulating a deletion button 1507. For example, the deletion button 1507 is pressed down, and thus, the GUI 1201 deletes the first correction parameter 1501 or the second correction parameter 1503.

A first correction threshold value 1511, for example, is the threshold value p in the description of FIG. 5. In FIG. 15, it is illustrated that "122.3" is set in a setting field 1512 of the threshold value.

A second correction threshold value 1513, for example, is the threshold value q in the description of FIG. 5. In FIG. 15, it is illustrated that "91.7" is set in a setting field 1514 of the threshold value.

Each of the correction threshold values can be increased by manipulating an addition button 1515. For example, the addition button 1515 is pressed down, and thus, the GUI 1201 newly displays a row of a third correction threshold value.

Each of the correction threshold values can be corrected by manipulating a correction button 1516. For example, the correction button 1516 is pressed down, and thus, the GUI 1201 sets the setting field 1512 of the first correction threshold value 1511 or the setting field 1514 of the second correction threshold value 1513 to be in a state where input is available, and receives the change of such setting values.

Further, each of the correction threshold values can be deleted by manipulating a deletion button 1517. For example, the deletion button 1517 is pressed down, and thus, the GUI 1201 deletes the first correction threshold value 1511 or the second correction threshold value 1513.

A graph 1521 before correction is an example of a graph illustrating the sensor data of the wearable sensor before the correction. In FIG. 15, the GUI 1201 displays a graph 1522 of the sensor data of the second finger and a graph 1523 of the sensor data of the first finger. In addition, the GUI 1201 displays index 1524 indicating which of such graphs is the graph 1522 of the of the sensor data of the second finger of the graph 1523 of the sensor data of the first finger.

A graph 1531 after correction is an example of a graph illustrating the sensor data of the wearable sensor after the correction. In FIG. 15, the GUI 1201 displays a graph 1532 of the sensor data of the second finger and a graph 1533 of the sensor data of the first finger. In addition, the GUI 1201 displays an index 1534 indicating which of such graphs is the graph 1532 of the sensor data of the second finger or the graph 1533 of the sensor data of the first finger.

In sensor state monitoring information 1541, whether the state of a wearable sensor that is registered is normal or abnormal is displayed. The GUI 1201 displays a sensor name that is registered in a sensor name 1542. The GUI 1201 displays the state of each wearable sensor corresponding to the sensor name 1542, registered in a state 1543. The GUI 1201 displays that the wearable sensor is normal in a case where the sensor is in a normal state, and the wearable sensor is abnormal in a case where the sensor is in an abnormal state. Note that, in a case where the wearable sensor is abnormal, information indicating an alert by the blink or the sound of the display may be output, and thus, a user may be notified or informed. In the determination of whether the wearable sensor is abnormal or normal, for example, it may be determined that the wearable sensor is abnormal in a case where the comparison unit 106 or the correction unit 107 determines that the sensed sensor data does not satisfy the reference value or in a case where it is determined that each divergence degree between the operation data and the standard glove operation data, between the operation data and the standard operation data, and between the operation data and the load cell operation data is greater than or equal to a constant reference, in addition to a case where the sensor data of the wearable sensor is not capable of being sensed. The comparison unit 106 or the correction unit 107 determines that it is not possible to perform the correction in the wearable sensor that is determined as abnormal, by using the correction parameter or the correction threshold value, and as described above, outputs that the wearable sensor is abnormal.

As described above, the information processing device 600 displays a parameter display portion for displaying the correction parameter described above (for example, the setting field 1502 of the first correction parameter 1501 or the setting field 1504 of the second correction parameter 1503), a sensor data display portion for displaying the sensor data before and after the correction (for example, the graph 1522 of the sensor data of the second finger before the correction, the graph 1523 of the sensor data of the first finger, the graph 1532 of the sensor data of the second finger after the correction, and the graph 1533 of the sensor data of the first finger), and a threshold value display portion for displaying the threshold value for determining that a predetermined motion is performed by using the wearable sensor (for example, the threshold value p and the threshold value q in the description of FIG. 5), on a display unit. Therefore, it is possible for the user to easily grasp a change before and after the correction according to not only a specific value of the set parameter or threshold value but also the setting values.

In addition, in the display unit described above, the information processing device 600 is capable of receiving the addition, the deletion, and the change of the parameter that is displayed in the parameter display portion and/or the threshold value that is displayed in the threshold value display portion. Therefore, it is possible for the user to grasp the setting value or the graph that is displayed, and then, to change the current setting value to a desirable setting value or to add or delete the parameter or the threshold value.

In addition, the information processing device 600 displays a state display portion representing whether or not the wearable sensor is in a correctable state (for example, the sensor state monitoring information 1541), on the display unit described above, and in a case where the wearable sensor is not in the correctable state, an alert (for example, information indicating that the wearable sensor is abnormal) in the state display portion described above. Therefore, it is possible for the user to grasp the abnormality of the wearable sensor at a glance.

FIG. 13 is an example of a case where the wearable sensor, a server, and the like are in the same factory or building, as a utilization example of the sensor data correction system illustrated in FIG. 6. In FIG. 13, a plurality of wearable sensors or standard motion mechanisms are provided in one factory, and wirelessly communicate with the information processing device 600 such as the server computer through a gateway 1301. According to such a configuration, even in the case of an environment in which an operation is performed by using the plurality of wearable sensors in the factory, the sensor data correction can be performed by one information processing device 600.

Figure 14:
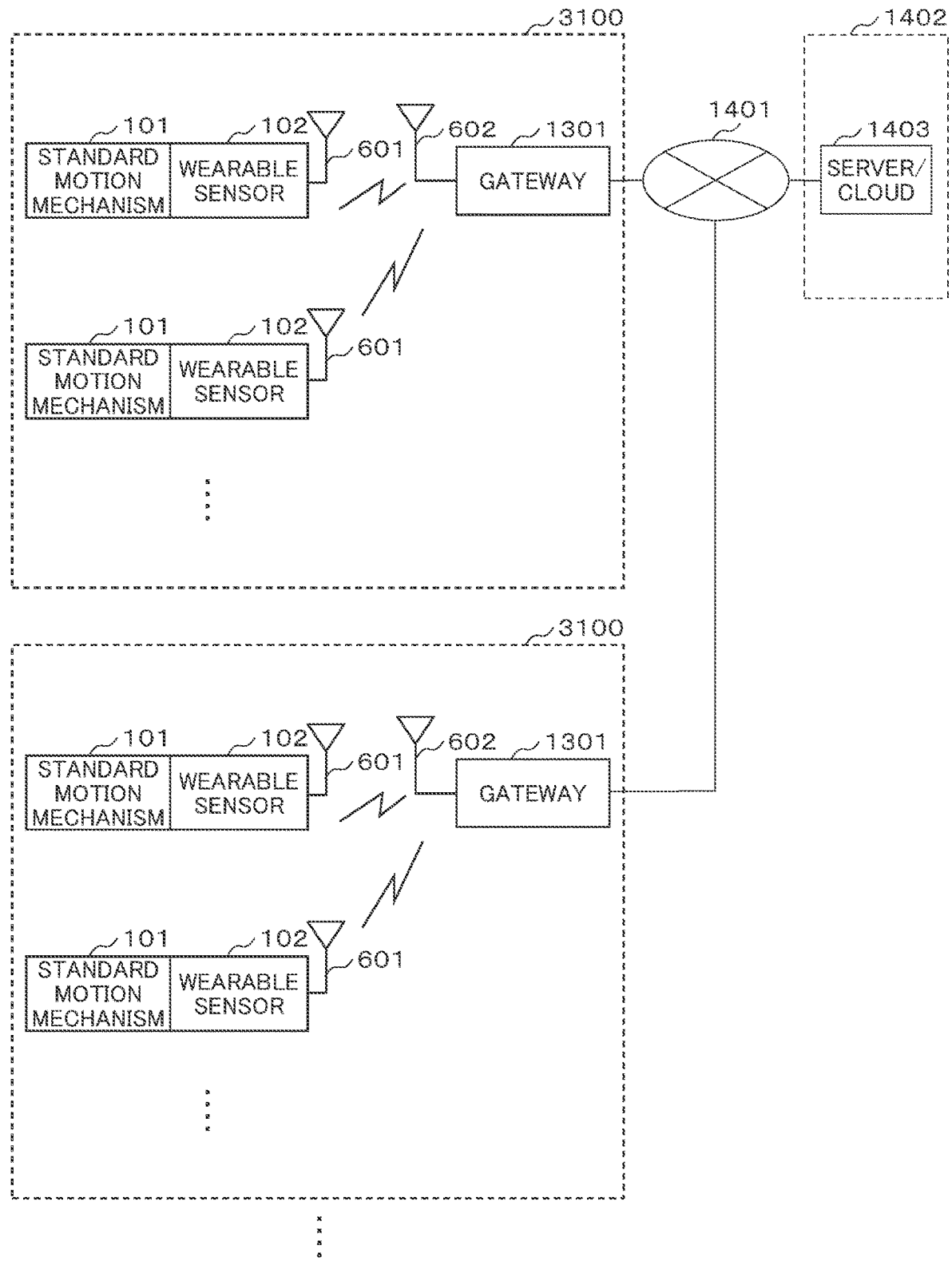
FIG. 14 is an example of a configuration when the wearable sensor, the gateway, and the server are not provided in the same factory or building, and the server is a so-called cloud.

FIG. 14 is an example of a case where the wearable sensor, the server, and the like are not provided in the same factory or building, and the server is a so-called cloud, as another utilization example of the sensor data correction system illustrated in FIG. 13. In FIG. 14, the gateway 1301 illustrated in FIG. 13 is connected to an external network 1401, and an information processing device 1403 such as a cloud or a server computer provided in an external system 1402 is also connected to the external network 1401. In the case of such a configuration, for example, it is possible to transmit sensor data acquired in each factory of a plurality of companies to a system of another company that manages a system, and to uniformly manage the sensor data of the wearable sensor of each of the companies, in another company.

As described above, in this system, the wearable sensor that is different at each time is mounted on the mechanism that consistently performs the standard operation motion with constant force adjustment, a constant direction, and a constant speed, and the standard motion is performed. The motion is consistently constant, and thus, a difference in the sensing data is reflected as the individual difference of each of the wearable sensors. In this system, the values of each of the wearable sensors are corrected on the basis of the individual difference properties.

Further, in this system, in the same individual wearable sensor, the standard operation motion and each personal motion data item are acquired, physical characteristics of an individual hand such as the size of the hand or the length of the finger, and motional characteristics of the personal hand such as the habit of a bending mode and a gripping mode of the finger are extracted, and the values of each of the wearable sensors are corrected on the basis of the personal properties.

According to such correction, it is possible to efficiently and accurately correct both of the individual difference of each of the wearable sensors and the personal properties of the wearable sensor that is worn by a person.

In addition, in the wearable sensor that senses the motion of the operator, there is a problem that the individual difference of the sensing data increases in accordance with a subtle difference at the time of built-in processing of the sensor, the individual properties of the sensor, or the like. In contrast, according to this mode, it is possible to perform sensing data correction with a high accuracy without an effort, and to easily deploy a reliable wearable sensor to various places and to reduce an operation load.

What is claimed is:

1. A sensor data correction system, comprising:
a moveable mount configured to mount thereon a wearable sensor, the moveable mount configured to move with a predetermined force in a constant direction and at a constant speed; and
a computer configured to:
wirelessly receive via a network first sensor data that is sensed by a first wearable sensor mounted on the moveable mount,
wirelessly receive via the network second sensor data that is sensed by a second wearable sensor mounted on the moveable mount, and
calculate a relationship between the first sensor data and the second sensor data, and
correct the first sensor data or the second sensor data based on the calculated relationship.

2. The sensor data correction system according to claim 1, wherein the computer is configured to:
calculate properties of the first wearable sensor by using the first sensor data in an operation zone of the first wearable sensor, and calculate properties of the second wearable sensor by using the second sensor data in a zone corresponding to the operation zone, and
perform a correction on the basis of the calculated relationship from the properties of the first wearable sensor and the properties of the second wearable sensor.

3. The sensor data correction system according to claim 2, wherein the computer is configured to:
set a threshold value for determining that a predetermined motion is performed by using the first wearable sensor or the second wearable sensor, based on a difference between the properties of the first wearable sensor and the properties of the second wearable sensor.

4. The sensor data correction system according to claim 1,
wherein the computer is configured to convert a motion that is sensed by the first wearable sensor or the second wearable sensor into a data signal, and
wherein the relationship is calculated using the data signal.

5. The sensor data correction system according to claim 1, further comprising:
a display unit coupled to the computer,
wherein the computer is configured to:
display on the display unit, a parameter display screen displaying a parameter for performing the correction, a sensor data display screen for displaying the first sensor data and the second sensor data before and after the correction, and a threshold value display screen for displaying a threshold value for determining that a predetermined motion is performed by using the first wearable sensor or the second wearable sensor.

6. The sensor data correction system according to claim 5, wherein the computer is configured to:
receive inputs of addition, deletion, and change of the parameter that is displayed in the parameter display screen and/or the threshold value that is displayed in the threshold value display screen.

7. The sensor data correction system according to claim 5, wherein the computer is configured to:
display on the display unit, a state display screen indicating whether the first wearable sensor or the second wearable sensor is in a correctable state, and
in a case where the first wearable sensor or the second wearable sensor is not in the correctable state, display an alert in the state display screen.

\* \* \* \* \*